United States Patent [19]

Baker et al.

[11] 4,050,923
[45] Sept. 27, 1977

[54] N-BENZYL-2-(3,5-DIMETHYL PHENOXY)-2-ALKOXY AMIDE HERBICIDES

[75] Inventors: Don R. Baker, Orinda; Francis H. Walker, Mill Valley, both of Calif.

[73] Assignee: Stauffer Chemical Company, Westport, Conn.

[21] Appl. No.: 591,686

[22] Filed: June 30, 1975

[51] Int. Cl.$^2$ .............................................. A01D 9/20
[52] U.S. Cl. .................................. 71/118; 260/559 B
[58] Field of Search .................. 71/118, 117, 116, 115, 71/110, 109, 108

[56] References Cited

U.S. PATENT DOCUMENTS

| | | | |
|---|---|---|---|
| 2,412,510 | 12/1946 | Jones | 71/118 |
| 3,277,160 | 10/1966 | Weil et al. | 71/118 X |
| 3,439,018 | 4/1969 | Brookes et al. | 71/118 X |
| 3,544,304 | 12/1970 | Soper | 71/107 |

OTHER PUBLICATIONS

Leaper et al., Chem. Abst., vol. 45, (1951) 7055c.

Primary Examiner—Lewis Gotts
Assistant Examiner—Catherine L. Mills
Attorney, Agent, or Firm—Edwin H. Baker

[57] ABSTRACT

N-benzyl-2-(3,5-dimethyl phenoxy)-2-alkoxy amide compounds having the formula

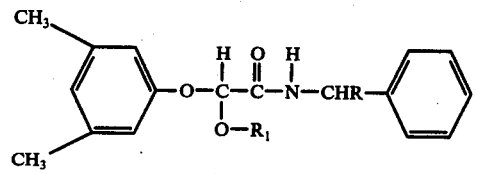

in which R is hydrogen or alkyl and $R_1$ is alkyl; and their use as herbicides.

3 Claims, No Drawings

N-BENZYL-2-(3,5-DIMETHYL PHENOXY)-2-ALKOXY AMIDE HERBICIDES

This invention relates to certain novel N-benzyl-2-(3,5-dimethyl phenoxy)-2-alkoxy amides which are useful as herbicides.

The compounds of the present invention are new compositions of matter and correspond to the formula

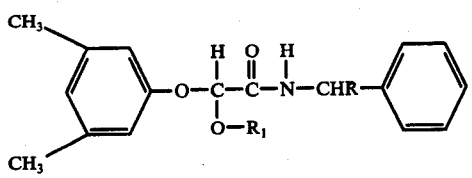

in which R is hydrogen or alkyl having 1 to 4 carbon atoms, preferably methyl and $R^1$ is alkyl having 1 to 4 carbon atoms, preferably 1 to 2 carbon atoms and more preferably ethyl.

In the above description of the compounds of this invention, alkyl includes both straight chain and branched chain configurations, for example, methyl, ethyl, n-propyl, isopropyl, n-butyl, sec.-butyl or tert.-butyl.

The compounds of this invention are active herbicides of a general type. That is, they are herbicidally effective against a wide range of plant species. The method of controlling undesirable vegetation of the present invention comprises applying an herbicidally effective amount of the above-described compounds to the area where control is desired.

An herbicide is used herein to mean a compound which controls or modifies the growth of plants. By a "growth controlling amount" is meant an amount of compound which causes a modifying effect upon the growth of plants. Such modifying effects include all deviations from natural development, for example, killing, retardation, defoliation, dessication, regulation, stunting, tillering, stimulation, dwarfing and the like. By "plants", it is meant germinating seeds, emerging seedlings, and established vegetation including the roots and above-ground portions.

The compounds of the present invention can be prepared by the following general method:

Reaction No. 1

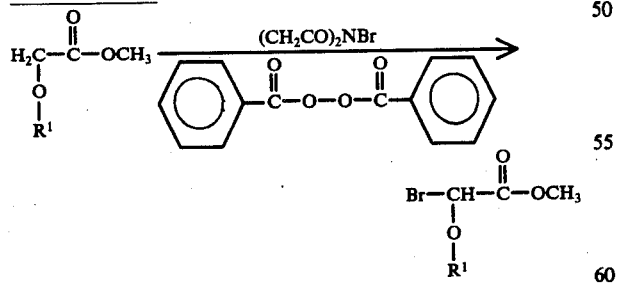

Generally, a mole amount of the ester, a slight mole excess of the succinimide, and a few crystals of the peroxide are mixed in carbon tetrachloride and heated to reflux for an hour. The mixture is then cooled and filtered and the filtrate is evaporated to leave an oil.

Reaction No. 2

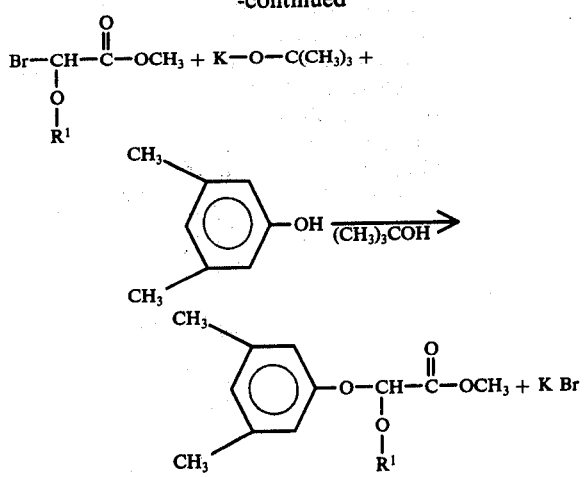

The potassium t-butoxide is first dissolved in t-butyl alcohol, followed by addition of the phenol and finally the ester, the latter two reactants approximately equal in molar quantity to the butoxide. In the ensuing exothermic reaction, the potassium bromide separates from the mixture which is subsequently poured into water and extracted with chloroform.

Reaction No. 3

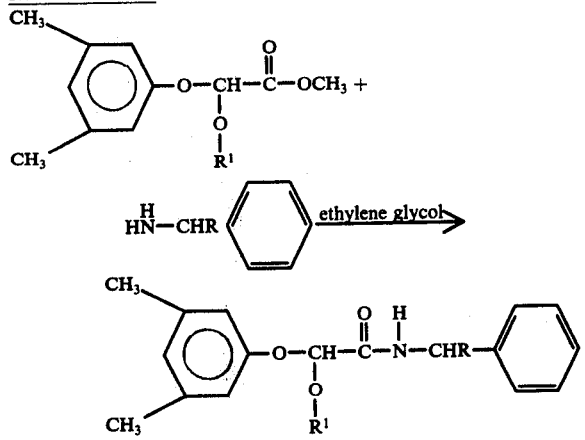

Generally, to a mole excess of the amine dissolved in a solvent along with a small amount of ethylene glycol is added the acetate. With slurring the mixture is heated at 50° C for about 3 hours and the product is recovered and recrystallized by conventional means.

The example hereinafter illustrates a method of preparation of the compounds of the invention.

EXAMPLE

N-benzyl-2-methoxy-2-(3,5-dimethylphenoxy)acetamide

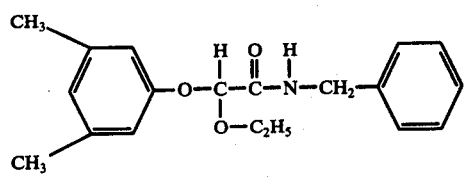

A mixture of 20.0 g (0.19 mole) methyl 2-methoxyacetate, 34.6 g (0.20 mole) N-bromosuccinimide and a few crystals of benzoyl peroxide in 200 ml carbon tetrachloride was heated to reflux. After an initial vigorous reaction, the mixture was heated for 1 hour, cooled, and filtered. The filtrate was evaporated at 15 mm pressure on a rotary evaporator to leave 34.0 g (98% yield) of an oil, $n_D^{30}$— 1.4694, identified by NMR analysis as methyl 2-bromo-2-methoxyacetate.

Potassium t-butoxide, 21.5 g (0.18 mole), was dissolved in 150 ml t-butyl alcohol. The mixture was stirred for 15 minutes at room temperature. 22.0 g (0.18 mole) of 3,5-dimethylphenol was then added, followed by 32.0 g (0.18 mole) of methyl 2-bromo-2-methoxyacetate. The addition occurred at 35°–40° C. The reaction was exothermic with separation of potassium bromide. After 3 hours of stirring with no external heating, the mixture was poured into 600 ml water and the resulting mixture was extracted with two 150 ml portions of chloroform. The extracts were combined and washed with three 150 ml portions of saturated sodium chloride solution. The solution was then dried over magnesium sulfate and evaporated to leave 29.9 g of an oil, $n_D^{30}$— 1.5013, identified by infrared spectroscopy as methyl-2-(3,5-dimethylphenoxy)-2-methoxyacetate.

In a 300 ml flask were placed 2.7 g (0.03 mole) benzyl amine and 1 ml of ethylene glycol. To this was added 5.0 g (0.02 mole) of the methyl-2-(3,5-dimethylphenoxy)-2-methoxyacetate with stirring. The temperature rose to 31° C and then began to decrease. The mixture was heated at 50° C for 3 hours and was then allowed to cool to room temperature. The partially solidified product was dissolved in 100 ml benzene and the resulting solution was washed with 3–100 ml portions of water. The solution was dried over magnesium sulfate and evaporated to leave a solid, 5.0 g which was recrystallized from hexane to give 3.8 g of a solid, m.p. 77°–79° C, which was identified by NMR spectroscopy to be the desired product.

Other compounds, such as those included in the following table, can be prepared in a manner analogous to that taught in the examples above, using the appropriate corresponding materials.

The following is a table of certain selected compounds that are preparable according to the procedure described hereto. Compound numbers are assigned to each compound and are used through the remainder of the application.

TABLE I

| Compound Number | R | R¹ | m.p. |
|---|---|---|---|
| 1* | H | CH₃ | 77–79° C |
| 2 | CH₃ | CH₃ | $n_D^{30}$ 1.5425 |

* Prepared in Example

Herbicidal Screening Tests

As previously mentioned, the herein described compounds produced in the above-described manner are phytotoxic compounds which are useful and valuable in controlling various plant species. Selected compounds of this invention are tested as herbicides in the following manner.

Pre-emergence Herbicide Screening Test

Using an analytical balance, 20 mg of the compound to be tested is weighed out on a piece of glassine weighing paper. The paper and compound are placed in a 30-ml wide-mouth bottle and 3 ml of acetone containing 1% Tween 20® is added to dissolve the compound. If the material is not soluble in acetone, another solvent such as water, alcohol or dimethylformamide (DMF) is used instead. When DMF is used, only 0.5 ml or less is used to dissolve the compound and then another solvent is used to make the volume up to 3 ml. The 3 ml of solution is sprayed uniformly on the soil contained in a small flat one day after planting weed seeds in the flat of soil. A No. 152 DeVilbiss atomizer is used to apply the spray using compressed air at a pressure of 5 lb/sq. in. The rate of application is 8 lb/acre and the spray volume is 143 gal/acre.

On the day preceding treatment, the flat which is 7 inches long, 5 inches wide and 2.75 inches deep is filled to a depth of 2 inches with loamy sand soil. Seeds of seven different weed species are planted in individual rows using one species per row across the width of the flat. The seeds are covered with soil so that they are planted at a depth of 0.5 inch. The seeds used are hairy crabgrass (*Digitaria sanguinalis*), green foxtail (*Setaria viridis*), watergrass (*Echinochloa crusgalli*), red oat (*Avena sativa*), redroot pigweed (*Amaranthus retroflexus*), Indian mustard (*Brassica juncea*) and curly dock (*Rumex crispus*). Ample seeds are planted to give about 20 to 50 seedlings per row after emergence depending on the size of the plants.

After treatment, the flats are placed in the greenhouse at a temperature of 70° to 85° F and watered by sprinkling. Two weeks after treatment, the degree of injury or control is determined by comparison with untreated check plants of the same age. The injury rating from 0 to 100% is recorded for each species as percent control with 0% representing no injury and 100% representing complete kill.

Post-emergence Herbicide Screening Test

Seeds of six plant species, including hairy crabgrass, watergrass, red oat, mustard, curly dock and Pinto beans (*l* Phaseolus vulgaris) are planted in the flats as described above for pre-emergence screening. The flats are placed in the greenhouse at 70° to 85° F and watered daily with a sprinkler. About 10 to 14 days after planting when the primary leaves of the bean plants are almost fully expanded and the first trifoliate leaves are just starting to form, the plants are sprayed. The spray is prepared by weighing out 20 mg of the test compound, dissolving it in 5 ml of acetone containing 1% Tween 20® and then adding 5 ml of water. The solution is sprayed on the foliage using a No. 152 DeVilbiss atomizer at an air pressure of 5 lb/sq. in. The spray concentration is 0.2% and the rate is 8 lb/acre. The spray volume is 476 gal/acre.

The results of these tests are shown in Table II.

TABLE II

| Compound Number | Herbicidal Activity - Screening Results * Percent Control at 8 lb/A | |
|---|---|---|
| | Pre-emergence | Post-emergence |
| 1 | 60 | 67 |
| 2 | 59 | 60 |

* Average for seven plant species in the pre-emergence test and for six plant species in the post-emergence test.

The compounds of the present invention are used as pre-emergence or post-emergence herbicides and are applied in a variety of ways at various concentrations. In practice, the compounds herein defined are formulated into herbicidal compositions, by admixture, in herbicidally effective amounts, with the adjuvants and carriers normally employed for facilitating the dispersion of active ingredients for agricultural applications, recognizing the fact that the formulation and mode of application of a toxicant may affect the activity of the materials in a given application. Thus, these active herbicidal compounds may be formulated as granules of relatively large particle size, as wettable powders, as emulsifiable concentrates, as powdery dusts, as solutions or as any of several other known types of formulations, depending upon the desired mode of application. Preferred formulations for both pre- and post-emergence herbicidal applications are wettable powders, emulsifiable concentrates and granules. These formulations may contain as little as about 0.5% to as much as about 95% or more by weight of active ingredient. The amount applied depends upon the nature of the seeds or plants to be controlled and the rate of application varies from ⅛ to approximately 50 pounds per acre.

Wettable powders are in the form of finely divided particles which disperse readily in water or other dispersant. The wettable powder is ultimately applied to the soil either as a dry dust or as a dispersion in water or other liquid. Typical carriers for wettable powders include fuller's earth, kaolin clays, silicas and other readily wet organic or inorganic diluents. Wettable powders normally are prepared to contain about 5 to about 95% of the active ingredient by weight and usually also contain a small amount of wetting, dispersing or emulsifying agent to facilitate wetting and dispersion.

Emulsifiable concentrates are homogeneous liquid compositions which are dispersible in water or other dispersant, and may consist entirely of the active compound with a liquid or solid emulsifying agent, or may also contain a liquid carrier, such as xylene, heavy aromatic naphthas, isophorone and other non-volatile organic solvents. For herbicidal application, these concentrates are dispersed in water or other liquid carrier and normally applied as a spray to the area to be treated. The percentage by weight of the essential active ingredient may vary according to the manner in which the composition is to be applied, but in general comprises about 0.5 to 95% of active ingredient by weight of the herbicidal composition.

Granular formulations, wherein the toxicant is carried on relatively coarse particles, are usually applied without dilution to the area in which suppression of vegetation is desired. Typical carriers for granular formulations include sand, fuller's earth, bentonite clays, vermiculite, perlite and other organic or inorganic materials which absorb or which may be coated with the toxicant. Granular formulations normally are prepared to contain about 5 to about 25% of active ingredient and may also contain small amounts of other ingredients which may include surface-active agents such as wetting agents, dispersing agents or emulsifiers; oils such as heavy aromatic naphthas, kerosene or other petroleum fractions, or vegetable oils; and/or stickers such as dextrins, glue or synthetic resins.

Typical wetting, dispersing or emulsifying agents used in agricultural formulations include, for example, the alkyl and alkylaryl sulfonates and sulfates and their sodium salts; polyhydric alcohols; and other types of surface-active agents, many of which are available in commerce. The surface-active agent, when used, normally comprises from 0.1 to 15% by weight of the herbicidal composition.

Dusts, which are free-flowing admixtures of the active ingredient with finely divided solids such as talc, clays, flours, and other organic and inorganic solids which act as dispersants and carriers for the toxicant, are useful formulations for soil-incorporating applications.

Pastes, which are homogeneous suspensions of a finely divided solid toxicant in a liquid carrier such as water or oil, are employed for specific purposes. These formulations normally contain about 5 to about 95% of active ingredient by weight, and may also contain small amounts of a wetting, dispersing or emulsifying agent to facilitate dispersion. For application, the pastes are normally diluted and applied as a spray to the area to be affected.

Other useful formulations for herbicidal applications include simple solutions of the active ingredient in a dispersant in which it is completely soluble at the desired concentration, such as acetone, alkylated naphthalenes, xylene or other organic solvents. Pressurized sprays, typically aerosols, wherein the active ingredient is dispersed in finely divided form as a result of vaporization of a low boiling dispersant solvent carrier, such as the Freons, may also be used.

The phytotoxic compositions of this invention are applied to the plants in the conventional manner. Thus, the dust and liquid compositions can be applied to the plant by the use of power-dusters, boom and hand sprayers and spray dusters. The compositions can also be applied from airplanes as a dust or a spray because they are effective in very low dosages. In order to modify or control growth of germinating seeds or emerging seedlings, as a typical example, the dust and liquid compositions are applied to the soil according to conventional methods and are distributed in the soil to a depth of at least ½ inch below the soil surface. It is not necessary that the phytotoxic compositions to be admixed with the soil particles since these compositions can also be applied merely by spraying or sprinkling the surface of the soil. The phytotoxic compositions of this invention can also be applied by addition to irrigation water supplied to the field to be treated. This method of application permits the penetration of the compositions into the soil as the water is absorbed therein. Dust compositions, granular compositions or liquid formulations applied to the surface of the soil can be distributed below the surface of the soil by conventional means such as discing, dragging or mixing operations.

The phytotoxic compositions of this invention can also contain other additaments, for example, fertilizers, pesticides and the like, used as adjuvants or in combination with any of the above-described adjuvants. Other phytotoxic compounds useful in combination with the above-described compounds include, for example, 2,4-dichlorophenoxyacetic acids, 2,4,5-trichlorophenoxyacetic acid, 2-methyl-4-chlorophenoxyacetic acid and the salts, esters and amides thereof; triazine derivatives, such as 2,4-bis(3-methoxypropylamino)-6-methylthio-s-triazine, 2-chloro-4-ethylamino-6-isopropylamino-s-triazine, and 2-ethylamino-4-isopropylamino-6-methylmercapto-s-triazine; urea derivatives, such as 3-(3,4-dichlorophenyl)-1,1-dimethyl urea and 3-(p-chlorophenyl)-1,1-dimethyl urea; and acetamides such as N,N-diallyl-α-chloroacetamide, and the like; benzoic acids such as 3-amino-2,5-dichlorobenzoic; thiocarbamates, such as S-propyl dipropylthiocarbamate, S-ethyl dipropylthiocarbamate, S-ethyl cyclohexylethyl thiocarbamate, S-ethyl hexahydro-1H-azepine-1-carbothioate and the like; 4-(methylsulfonyl)-2,6-dinitro-N,N-substituted anilines, such as 4-(methylsulfonyl)-2,6-dinitro-N,N-di-n-propyl aniline, 4-trifluoromethyl-2,6-dinitro-N,N-substituted anilines, such as 4-trifluoromethyl-2,6-dinitro-N,N-di-n-propyl aniline and 4-trifluoromethyl-2,6-dinitro-N-ethyl-N-n-butyl aniline. Fertilizers useful in combination with the active ingredients include, for example, ammonium nitrate, urea and superphosphate. Other useful additaments include materials in which plant organisms take root and grow such as compost, manure, humus, sand and the like.

The concentration of a compound of the present invention, constituting an effective amount of the best mode of administration in the utility disclosed is readily determinable by those skilled in the art.

It is claimed:

1. The method of controlling undesirable vegetation which comprises applying to the area where control of said vegetative growth is desired, an herbicidal amount of a compound having the formula

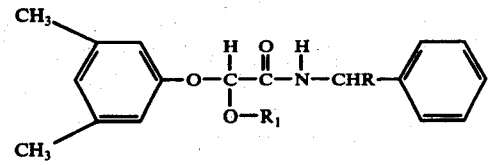

in which R is hydrogen or alkyl having 1 to 4 carbon atoms and $R^1$ is alkyl having 1 to 4 carbon atoms.

2. The method of claim 1 in which R is methyl and $R^1$ is methyl.

3. The method of claim 1 in which R is hydrogen and $R^1$ is methyl.

* * * * *